(12) United States Patent
Van Antwerp et al.

(10) Patent No.: US 6,368,274 B1
(45) Date of Patent: Apr. 9, 2002

(54) REUSABLE ANALYTE SENSOR SITE AND METHOD OF USING THE SAME

(75) Inventors: William P. Van Antwerp, Valencia; John J. Mastrototaro, Los Angeles, both of CA (US)

(73) Assignee: Medtronic Minimed, Inc., Northridge, CA (US)

( * ) Notice: Subject to any disclaimer, the term of this patent is extended or adjusted under 35 U.S.C. 154(b) by 0 days.

(21) Appl. No.: 09/566,027

(22) Filed: May 8, 2000

Related U.S. Application Data

(60) Provisional application No. 60/141,935, filed on Jul. 1, 1999.

(51) Int. Cl.[7] ................................................ A61B 5/05
(52) U.S. Cl. ........................................ 600/365; 600/309
(58) Field of Search ................................ 600/345, 346, 600/347, 348, 365, 300, 301, 309, 372, 373, 374, 375, 377; 128/899

(56) References Cited

U.S. PATENT DOCUMENTS

| | | | |
|---|---|---|---|
| 4,140,963 A | * 2/1979 | Rao et al. .................... 600/309 |
| 4,240,438 A | 12/1980 | Updike et al. ............... 128/635 |
| 4,757,022 A | 7/1988 | Shults et al. ................. 435/291 |
| 4,986,271 A | 1/1991 | Wilkins ........................ 128/635 |
| 4,994,167 A | 2/1991 | Shults et al. ................ 204/403 |
| 5,431,160 A | 7/1995 | Wilkins ........................ 128/635 |
| 5,476,776 A | 12/1995 | Wilkins ....................... 435/176 |
| 5,651,767 A | * 7/1997 | Schulman et al. ........... 600/372 |

* cited by examiner

Primary Examiner—Kevin Shaver
Assistant Examiner—Navin Natnithithadha
(74) Attorney, Agent, or Firm—Medtronic Minimed, Inc.

(57) ABSTRACT

A reusable analyte sensor site for use with a replaceable analyte sensor for determining a level of an analyte includes a site housing. Preferably, the site housing material is formed to have an interior cavity with an opening and a conduit that is connected to the opening of the interior tissue ingrowth and vasuclarization, and yet be free of tissue ingress. Also, the site housing material permits the analyte to pass through the site housing material to the interior cavity to permit measurement by the replaceable analyte sensor. In addition, the conduit has a predetermined length to inhibit trauma and encapsulation of tissue occurring at the conduit, which is associated with placing the replaceable analyte sensor in the interior cavity of the site housing, from interfering with the tissue ingrowth and vasuclarization surrounding the interior cavity of the site housing material.

16 Claims, 2 Drawing Sheets

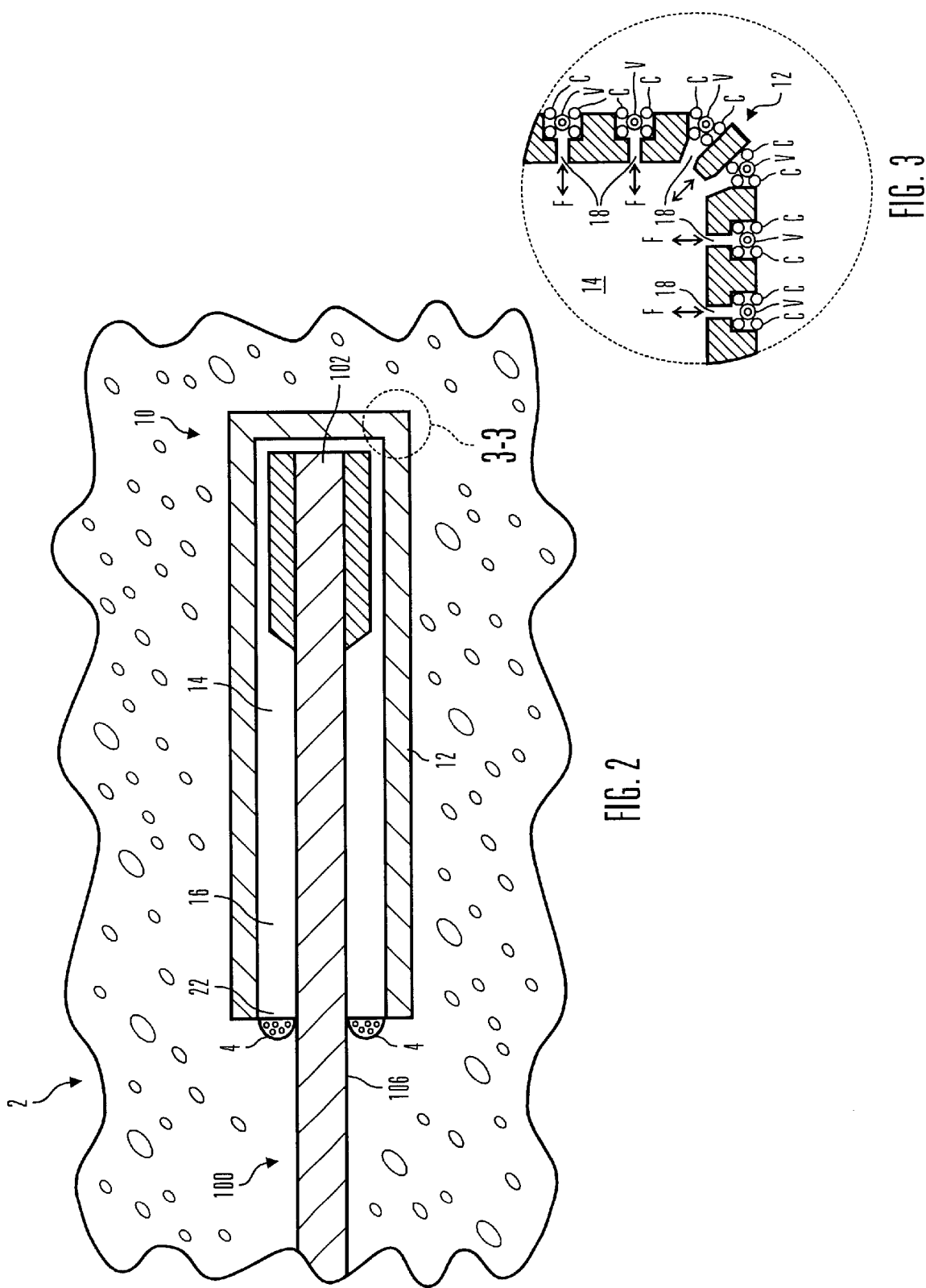

REUSABLE ANALYTE SENSOR SITE AND METHOD OF USING THE SAME

RELATED APPLICATIONS

This application claims priority on U.S. Provisional Application Serial No. 60/141,935 filed Jul. 1, 1999 and entitled "Reusable Analyte Sensor Site And Method Of Using The Same", which is herein specifically incorporated by reference.

FIELD OF THE INVENTION

This invention relates to reusable analyte sensor sites for use with replaceable, long term implantable anlayte sensors, in particular embodiments, to reusable glucose sensor sites for use with replaceable, long term glucose sensors.

BACKGROUND OF THE INVENTION

Over the years, bodily characteristics have been determined by obtaining a sample of bodily fluid. For example, diabetics often test for blood glucose levels with a blood glucose meter. Traditional blood glucose determinations have utilized a painfull finger prick using a lancet to withdraw a small blood sample that is used by the blood glucose meter. This results in discomfort from the lancet as it contacts nerves in the subcutaneous tissue. The pain of lancing and the cumulative discomfort from multiple needle pricks is a strong reason why patients fail to comply with a medical testing regimen used to determine a change in characteristic over a period of time. In addition, these blood glucose meters are only designed to provide data at discrete points and do not provide continuous data to show the variations in the characteristic between testing times.

A variety of subcutaneous electrochemical sensors for use with monitors have been developed for detecting and/or quantifying specific agents or compositions in a patient's blood. For instance, glucose sensors have been developed for use in obtaining an indication of blood glucose levels in a diabetic patient. Such readings are useful in monitoring and/or adjusting a treatment regimen which typically includes the regular administration of insulin to the patient. Thus, blood glucose readings from the monitor improve medical therapies with semi-automated medication infusion pumps of the external type, as generally described in U.S. Pat. Nos. 4,562,751; 4,678,408; and 4,685,903, which are herein incorporated by reference. Typical thin film sensors are described in commonly assigned U.S. Pat. Nos. 5,390,671; 5,391,250; 5,482,473; and 5,586,553 which are incorporated by reference herein. However, the thin film subcutaneous glucose sensors must be changed every few days to prevent infection. Also, due to the small size of these sensors to minimize pain on insertion under the skin, the enzyme wear out relatively quickly and require regular replacement. In addition, the user must carry around external hardware connected or linked to the sensor. Thus, although subcutaneous sensors provide an improvement over conventional test strips, they still require frequent changes.

Long term implanted glucose sensors have been proposed that can stay in the body for long periods of time, such as weeks and months. These long term implanted glucose sensors are particularly well adapted for use with automated implantable medication infusion pumps, as generally described in U.S. Pat. No. 4,573,994, which is herein incorporated by reference. The long term glucose sensor would obviate the need for frequent replacement of sensors and the need to carry around a large amount of external equipment. However, the insertion and placement of long term sensors is more invasive to the body then other sensor technologies and it often causes trauma during the insertion of the long term sensor into the body. After insertion, the long term sensor would not be usable for a period of time until the body heals and vascularizes the implanted long term sensor. Thus, each time a long term sensor is replaced the body must re-vascularize the replaced sensor. Another drawback to long term sensors is the development of scar tissue that encapsulates the implanted sensor and inhibits the proper operation of the long term sensor. Therefore, materials must be carefully selected to promote vasularization and not encapsulation. This requires careful construction of the outer covering for the long term sensor, which increases costs and may further delay the period of time before a newly implanted sensor may be used.

SUMMARY OF THE DISCLOSURE

It is an object of an embodiment of the present invention to provide an improved reusable analyte sensor site, which obviates for practical purposes, the above mentioned limitations.

According to an embodiment of the invention, a reusable analyte sensor site for use with a replaceable analyte sensor for determining a level of an analyte includes a site housing. Preferably, the site housing material is formed to have an interior cavity with an opening and a conduit that is connected to the opening of the interior cavity to provide access to the interior cavity. The site housing material is selected to promote tissue ingrowth and vasuclarization, and yet be free of tissue ingress. Also, the site housing material permits the analyte to pass through the site housing material to the interior cavity to permit measurement by the replaceable analyte sensor. In addition, the conduit has a predetermined length to inhibit trauma and encapsulation of tissue occurring at the conduit, which is associated with placing the replaceable analyte sensor in the interior cavity of the site housing, from interfering with the tissue ingrowth and vascularization surrounding the interior cavity of the site housing material.

In particular embodiments, the conduit has a length of at least 5 millimeters, and the site housing material has a porosity in a range from 2 to 25 microns. Preferably, the site housing is for implantation into sub-dermal tissue and/or inter-peritoneal tissue. Also, the site housing material is selected from a group of materials consisting essentially of Teflon and Dacron. In addition, the site housing is chosen so that it will last for a period of time such that it can be used with two or more consecutive replaceable analyte sensors.

Preferred embodiments utilize a site housing material that passes glucose, and the replaceable analyte sensor is a glucose sensor. In other embodiments, the invention is embodied in a system that uses a replaceable analyte sensor with the reusable analyte sensor site. In alternative embodiments, the reusable analyte sensor site may be used with a replaceable infusion catheter for infusion a fluid into the body of a user.

Other features and advantages of the invention will become apparent from the following detailed description, taken in conjunction with the accompanying drawings which illustrate, by way of example, various features of embodiments of the invention.

BRIEF DESCRIPTION OF THE DRAWINGS

A detailed description of embodiments of the invention will be made with reference to the accompanying drawings, wherein like numerals designate corresponding parts in the several figures.

FIG. 2 is a partial cross-sectional diagram of the reusable analyte sensor site as shown along the line 2—2 in FIG. 1.

FIG. 3 is an enlarged cross-sectional view of the reusable sensor site as shown within the circle 3—3 in FIG. 2.

DETAILED DESCRIPTION OF THE PREFERRED EMBODIMENTS

Figure 1:
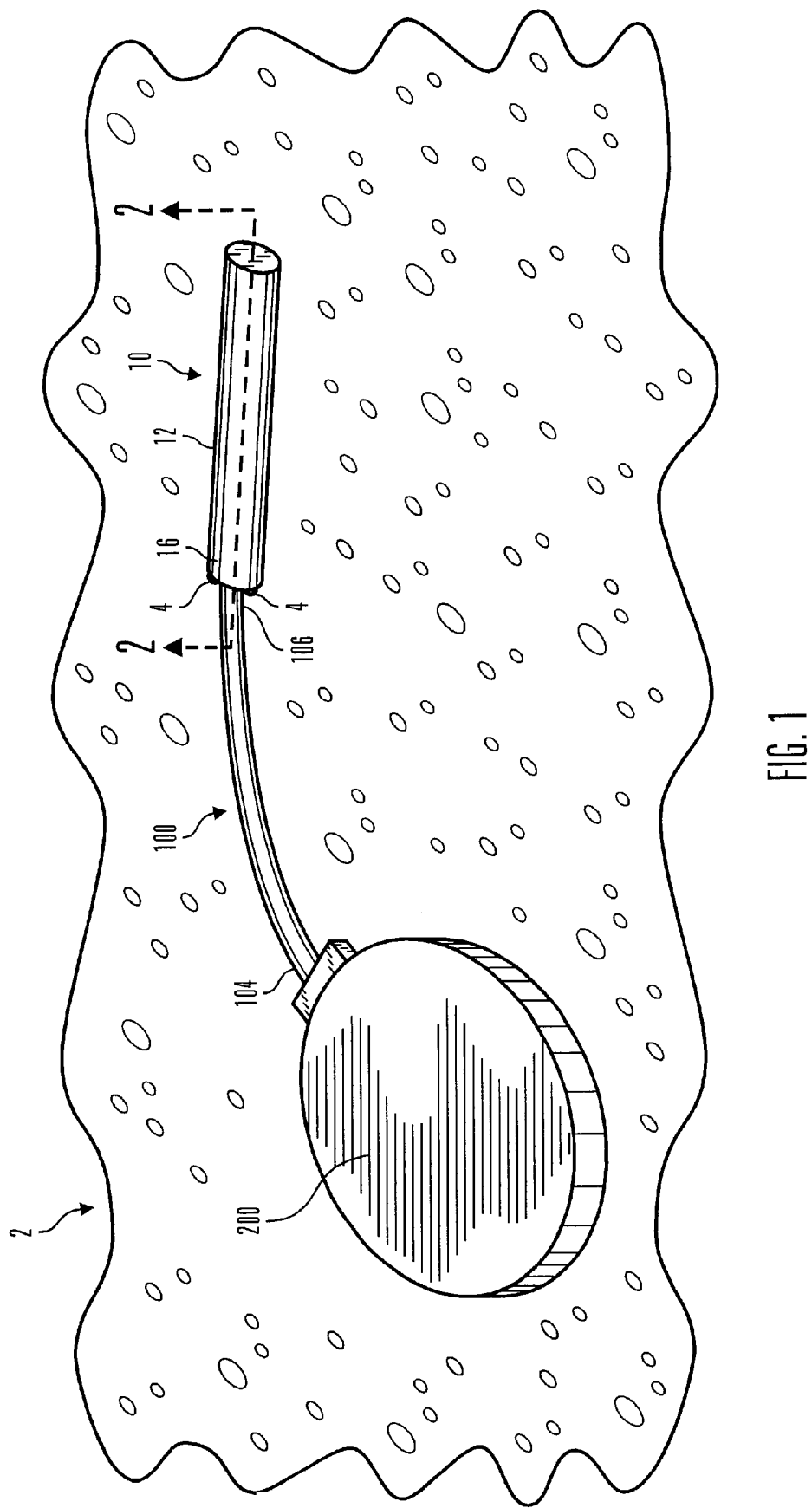
FIG. 1 is a perspective view of a reusable analyte sensor site and sensor monitor in accordance with an embodiment of the present invention.

As shown in the drawings for purposes of illustration, the invention is embodied in a reusable analyte sensor site that is used with a replaceable analyte sensor that determines body characteristics on a continuous, intermittent or near continuous basis. In preferred embodiments of the present invention, the replaceable analyte sensor is for determining glucose levels in the blood and/or bodily fluids of the user. However, it will be recognized that further embodiments of the invention may be used to determine the levels of other agents, characteristics or compositions, such as hormones, cholesterol, medications concentrations, viral loads (e.g., HIV), or the like. The reusable analyte sensor site and replaceable analyte sensor are primarily adapted for use in sub-dermal or inter-peritoneal human tissue. However, still further embodiments may be placed in other types tissue, such as muscle, lymph, organ tissue, veins, arteries or the like, and used in animal tissue. In other embodiments, the reusable analyte sensor site may be used with a medication or fluid infusion catheter that requires regular replacement.

As shown in FIGS. 1–3, the reusable analyte sensor site 10 in accordance with a preferred embodiments of the present invention includes a site housing 12 that is implanted in sub-dermal or inter-peritoneal tissue 2. Initially, the implanted site housing 12 is sutured in position by sutures (not shown). Preferably, the sutures are absorbable by the body. However, in alternative embodiments, the sutures are permanent.

In preferred embodiments, the material of the site housing 12 is formed to create an interior cavity 14 to support an ingrown and vascularized tissue (see FIGS. 2 and 3) structure around a replaceable analyte sensor 100. In addition to the interior cavity 14, the site housing 12 will form a conduit 16 that provides an entrance from the body tissue 2 to the interior cavity 14 of the site housing 12. The conduit 16 should be sized long enough so that the trauma associated with inserting and replacing the replaceable analyte sensor 100 (or catheter) will not effect the ingrown and vascularized tissue structure formed around the interior cavity 14 and an active sensing portion 102 of the replaceable analyte sensor 100 (or the outlet port of the replaceable catheter). Preferably, the length of the conduit is 5 millimeters. However, larger or smaller lengths (ranging from 2 millimeters 20 millimeters or more) may be used with the selection being dependent on the size of the site housing 12, the type of tissue 2 the site housing 12 is implanted in, the frequency within which the replaceable analyte sensor 100 (or replaceable catheter) must be replaced, or the like. Preferred embodiments of the site housing 12 can remain implanted in the tissue between 1 to 2 years. However, the actual long term life of the reusable analyte sensor site 10 will be a function of the material, the surface texture, the chemistry and the type of tissue 2 the reusable analyte sensor site 10 is implanted in. The goal is to achieve a reusable analyte sensor site 10 that is stable for multiple use to minimize the effects of frequent sensor replacement.

Preferably, the site housing 12 is formed from textured Teflon® or Dacron® that has a porosity selected to allow tissue ingrowth (i.e., cellular attachment) and vascularization of the material of the site housing 12. Many suitable materials are available from Gore & Associates Inc. and/or Baxter International. In alternative embodiments, other materials may be used, such as glass, sintered or woven metal meshes (e.g., titanium or other bio-compatible metal), composites, laminates, or the like, as long as they provide good vascularization and ingrowth of tissue. In preferred embodiments, the porosity (or mesh) size of the selected material is selected to be between 2–25 microns. However, in alternative embodiments, the porosity may be selected to be other sizes such that cells can attach and vascularization will occur. However, the porosity (or mesh) size must be selected to inhibit tissue ingress and keep tissue cells away from the active sensing portion 102 of the replaceable analyte sensor 100. Also, the sizing must be selected to avoid, or substantially minimize formation of a Fibrin sheath that attaches to the material of the site housing 12 or which causes encapsulation of the site housing 12. For example, as shown in FIG. 3, the porosity of the material of the site housing 12 is selected to promote cellular attachment of cells C to the mesh pores so as to encourage the vascularization of the site housing 12 with capillary vessels V to assure a good supply of bodily fluid F in and around the active sensing portion 102 of the replaceable analyte sensor 100 (or catheter), while at the same time inhibiting the ingress of tissues and cells C.

In addition to promoting tissue ingrowth and vascularization, the material used to form the site housing 12 must be sufficiently permeable to the analyte which is to be measured by the active sensing portion 102 of the replaceable analyte sensor 100. For instance, if glucose levels are being measured, the ingrown and vascularized site housing 12 must pass glucose (and transporting fluids) from the tissue 2 to the active sensing portion 102 of the replaceable analyte sensor 100 so that the glucose levels can be measured. Alternatively, if a replaceable catheter (not shown) is being used, such as for example to deliver insulin, the ingrown and vascularized site housing 12 must pass insulin out of the interior cavity 14 into the tissue 2. In particular embodiments, the material of the site housing 12 may also be selected to keep out certain materials or bodily fluid constituents that could interfere with or alter the readings of the active sensing portion 102 of the replaceable analyte sensor 100. It is further preferred that the material of the site housing 12 be selected so that any by products given off by the analyte sensing reaction will pass through the vascularized site housing and removed by the body of the user. In alternative embodiments, the material of the site housing 12 will be selected to pass the analyte but to contain any materials, or by products, produced by the replaceable analyte sensor 100.

As shown in FIG. 2 the interior cavity 14 of the site housing 12 is selected to be sufficiently large to accommodate the active sensing portion 102 of the replaceable analyte sensor 100 (or replaceable catheter). However, the interior cavity 14 should not be so large that the fluid within the interior cavity 14 (i.e., passed through the vascularized site housing 12) becomes stagnant. It is important that the fluid within the interior cavity 14 change frequently to provide an accurate reading on the active sensing portion 102 of the replaceable analyte sensor 100.

In preferred embodiments of the present invention, the replaceable analyte sensor is a electrochemical sensor that uses either enzymatic or fluorescent techniques to determine the analyte level. In the illustrated embodiments, the active sensing portion 102 of the replaceable analyte sensor 100 is inserted through the conduit 16 of the site housing 12 and slid into the interior cavity 14 of the site housing 12 to take analyte level readings. A connection end 104 of the replaceable analyte sensor 100 is generally attached to an analyte monitor 200 that is implanted in the body tissues 2 of the user. Preferably, the analyte monitor 200 transmits the signal values, raw data, operational information and parameters, or the like, to an external information retrieving device (not shown) or another implanted medical device (not shown). In alternative embodiments, the analyte monitor 200 may be incorporated into an implantable medication (or fluid) delivery pump, such as discussed above. Although it is possible to have the connection end 104 of the replaceable analyte sensor 100 extend outside of the body, this approach is not preferred due to the risk of infection, irritation, the possible inconvenience of having external connections, or the like.

Once in place, the traumatized tissue 4 around the conduit entrance 22 will tend to attach and encapsulate the entrance 22 to the conduit that opens out to the body tissue 2 and the mid-portion 106 of the replaceable analyte sensor 100 that is not within the interior cavity 14 of the site housing 12. This also tends to bind the entrance 22 of the conduit 16 to the mid-portion 106 of the replaceable analyte sensor 100. However, due to the length of the conduit 16 and the distance from of the traumatized tissue from the interior cavity 14, there is little, or no, trauma and encapsulation that will occur around the already established interior cavity 14 of the site housing 12. Thus, the active sensing portion 102 can begin to take readings relatively soon after implantation, stabilization and calibration of the replaceable analyte sensor 100. The entrance 22 of the conduit and the mid-portion 106 of the replaceable analyte sensor 100 that are encapsulated do not present an issue, since they do not effect operation of the active sensing portion 102 of the replaceable analyte sensor 100. When the replaceable analyte sensor 100 is replaced, the encapsulation and tissue attachment 4 around the entrance 22 of the conduit 16 is cut to free the replaceable analyte sensor 100, after which the replaceable analyte sensor 100 is withdrawn from the conduit 16 and interior cavity 14 of the site housing 12. The removal process causes trauma around the entrance 22 of the conduit 16; however, it does not traumatize the interior cavity 14, since it is located a sufficient distance away from the entrance 22 of the conduit 16 to avoid the effects of the new trauma. After removal of the old replaceable analyte sensor 100, a new replaceable analyte sensor 100 is inserted through the conduit 16 and into the interior cavity 14 of the site housing 12.

As discussed preferred embodiments of the replaceable analyte sensor 100 are electrochemical in nature. For instance, the sensor may use electrodes and glucose oxidase to measure the glucose levels in the bodily fluids. Examples of electrochemical sensors is shown and described in U.S. Pat. No. 5,391,250; No. 5,390,671, to Lord et al., entitled "Transcutaneous Sensor Insertion Set"; No. 5,165,407, to Wilson et al., entitled "Implantable Glucose Sensor"; and No. 4,890,620, to Gough, entitled "Two-Dimensional Diffusion Glucose Substrate Sensing Electrode", which are incorporated herein in their entireties by reference. Alternative embodiments may utilize optical properties such as shown and described in U.S. Patent No. 5,605,152, to Lord et al., entitled "Optical Glucose Sensor" or fiber optic structures and/or optical/fluorescent compounds such as shown and described in U.S. patent application Ser. No. 08/752,945 (corresponding to PCT/US96/18720), to Van Antwerp et al., entitled "Detection of Biological Molecules Using Chemical Amplification and Optical Sensor", all of which are herein incorporated by reference. Other sensor technologies suitable for implantation and working with bodily fluids are acceptable for use with the reusable analyte sensor site 10.

In alternative embodiments, the replaceable analyte sensor does not need to extend outside and beyond the entrance 22 of the conduit 16. For instance, the replaceable analyte sensor may be in the form of a patch that is placed inside the interior cavity 14 and integrated by light transmitted through the skin. In this situation, the entrance 22 of the conduit 16 would be capped and uncapped to provide access to the replaceable analyte sensor and the interior cavity 14. In another alternative embodiment, the entrance 22 of the conduit 16 is covered by a pierceable septum, or the like, and analyte sensor material, such as contained in microspheres, gels, or the like, is injected through the conduit 16 into the interior cavity 14, and withdrawn (if necessary) by the same route when new sensor material is to be placed into the interior cavity 14.

While the description above refers to particular embodiments of the present invention, it will be understood that many modifications may be made without departing from the spirit thereof. The accompanying claims are intended to cover such modifications as would fall within the true scope and spirit of the present invention.

The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed is:

1. A reusable analyte sensor site for use with a replaceable analyte sensor for determining a level of an analyte, the site comprising:

a site housing material formed to have an interior cavity with an opening and a conduit that is connected to the opening of the interior cavity to provide access to the interior cavity, wherein the site housing material is selected to promote tissue ingrowth and vasuclarization and be free of tissue ingress, wherein the site housing material permits the analyte to pass through the site housing material to the interior cavity to permit measurement by the replaceable analyte sensor, and wherein the conduit has a predetermined length to inhibit trauma and encapsulation of tissue occurring at the conduit, associated with placing the replaceable analyte sensor in the interior cavity of the site housing, from interfering with the tissue ingrowth and vascularization surrounding the interior cavity of the site housing material.

2. A site according to claim 1, wherein the conduit has a length of at least 5 millimeters.

3. A site according to claim 1, wherein the site housing material has a porosity in a range from 2 to 25 microns.

4. A site according to claim 1, wherein the site housing is for implantation into sub-dermal tissue.

5. A site according to claim 1, wherein the site housing is for implantation into inter-peritoneal tissue.

6. A site according to claim 1, wherein the site housing material is selected from a group of materials consisting essentially of Teflon and Dacron.

7. A site according to claim 1, wherein the site housing will last for a period of time such that it can be used with two or more consecutive replaceable analyte sensors.

8. A site according to claim 1, wherein the site housing material passes glucose, and wherein the replaceable analyte sensor is a glucose sensor.

9. A system for measuring analyte in a body of a user, the system comprising:
   a replaceable analyte sensor for determining a level of an analyte; and
   a reusable analyte sensor site made from a site housing material formed to have an interior cavity with an opening and a conduit that is connected to the opening of the interior cavity to provide access to the interior cavity, wherein the site housing material is selected to promote tissue ingrowth and vasuclarization and be free of tissue ingress, wherein the site housing material permits the analyte to pass through the site housing material to the interior cavity to permit measurement by the replaceable analyte sensor, and wherein the conduit has a predetermined length to inhibit trauma and encapsulation of tissue occurring at the conduit, and associated with placing the replaceable analyte sensor in the interior cavity of the site housing, from interfering with the tissue ingrowth and vascularization surrounding the interior cavity of the site housing material.

10. A system according to claim 9, wherein the conduit has a length of at least 5 millimeters.

11. A system according to claim 9, wherein the site housing material has a porosity in a range from 2 to 25 microns.

12. A system according to claim 9, wherein the reusable analyte sensor site is for implantation into sub-dermal tissue.

13. A system according to claim 9, wherein the reusable analyte sensor site is for implantation into inter-peritoneal tissue.

14. A system according to claim 9, wherein the reusable analyte sensor site housing material is selected from a group of materials consisting essentially of Teflon and Dacron.

15. A system according to claim 9, wherein the reusable analyte sensor site will last for a period of time such that it can be used with two or more consecutive replaceable analyte sensors.

16. A system according to claim 9, wherein the site housing material passes glucose, and wherein the replaceable analyte sensor is a glucose sensor.

* * * * *